United States Patent
Wu (10) Patent No.: US 11,744,462 B2
(45) Date of Patent: Sep. 5, 2023

(54) HEAD-MOUNTED VISION DETECTION EQUIPMENT, VISION DETECTION METHOD AND ELECTRONIC DEVICE

(71) Applicant: QINGDAO PICO TECHNOLOGY CO., LTD., Shandong (CN)

(72) Inventor: Tao Wu, Shandong (CN)

(73) Assignee: QINGDAO PICO TECHNOLOGY CO., LTD., Qingdao (CN)

( * ) Notice: Subject to any disclaimer, the term of this patent is extended or adjusted under 35 U.S.C. 154(b) by 0 days.

(21) Appl. No.: 17/880,901

(22) Filed: Aug. 4, 2022

(65) Prior Publication Data

US 2022/0369924 A1 Nov. 24, 2022

Related U.S. Application Data (63) Continuation of application No. PCT/CN2021/123608, filed on Oct. 13, 2021.

(30) Foreign Application Priority Data

Mar. 15, 2021 (CN) .......................... 202110278476.1

(51) Int. Cl.
*A61B 3/14* (2006.01)
*A61B 90/00* (2016.01)
(Continued)

(52) U.S. Cl.
CPC ................ *A61B 3/14* (2013.01); *A61B 3/005* (2013.01); *A61B 3/107* (2013.01); *A61B 90/36* (2016.02);
(Continued)

(58) Field of Classification Search
CPC ........... A61B 3/14; A61B 3/005; A61B 3/107; A61B 90/36; A61B 2090/365;
(Continued)

(56) References Cited

U.S. PATENT DOCUMENTS

| 11,087,029 | B1* | 8/2021 | Satpathy ............... H04L 9/0668 |
| 2004/0105073 | A1 | 6/2004 | Maddalena et al. |

(Continued)

FOREIGN PATENT DOCUMENTS

| CN | 102697525 A | 10/2012 |
| CN | 103190883 A | 7/2013 |

(Continued)

OTHER PUBLICATIONS

International Search Report dated Jan. 14, 2022 in International Patent Application No. PCT/CN2021/123608.

(Continued)

*Primary Examiner* — Mohammed A Hasan (57) ABSTRACT

The present disclosure relates to head-mounted vision detection equipment, vision detection method and electronic equipment, which relates to the technical field of vision detection. The head-mounted vision detection equipment includes a virtual reality headset, a sound collection device and a fundus detection device that are arranged on the virtual reality headset, and a processor. The vision detection headset is configured to display content to be recognized under control of the processor; the sound collection device is configured to obtain a recognition voice of a wearer for the content to be recognized; the fundus detection device is configured to obtain a fundus image of the wearer; and the processor is configured to acquire the recognition voice and the fundus image.

20 Claims, 3 Drawing Sheets

(51) Int. Cl.
*A61B 3/00* (2006.01)
*A61B 3/107* (2006.01)
*G06F 3/16* (2006.01)

(52) U.S. Cl.
CPC ........ *G06F 3/167* (2013.01); *A61B 2090/365* (2016.02)

(58) Field of Classification Search
CPC ..... A61B 3/152; A61B 3/0016; A61B 3/0033; A61B 3/0041; A61B 3/12; A61B 8/10; A61B 8/40; A61B 8/4209; A61B 8/44; A61B 8/52; A61B 8/54; G06F 3/167
USPC .......................................................... 351/206
See application file for complete search history.

(56) References Cited

U.S. PATENT DOCUMENTS

| | | | |
|---|---|---|---|
| 2014/0243614 A1* | 8/2014 | Rothberg | A61B 5/318 600/407 |
| 2016/0270656 A1* | 9/2016 | Samec | A61B 5/398 |
| 2017/0173262 A1* | 6/2017 | Veltz | G16H 20/17 |
| 2017/0184847 A1* | 6/2017 | Petrov | H04N 5/2256 |
| 2018/0008141 A1 | 1/2018 | Krueger | |
| 2018/0136486 A1 | 5/2018 | Macnamara et al. | |
| 2018/0317832 A1 | 11/2018 | Scott | |
| 2019/0014981 A1 | 1/2019 | Hooriani et al. | |
| 2019/0175011 A1 | 6/2019 | Jensen et al. | |
| 2020/0008667 A1 | 1/2020 | Raviv et al. | |
| 2020/0029802 A1 | 1/2020 | Lane et al. | |
| 2020/0384475 A1* | 12/2020 | Carty | B01L 3/5453 |
| 2021/0030270 A1 | 2/2021 | Goyal et al. | |
| 2021/0048686 A1 | 2/2021 | Muschielok et al. | |
| 2022/0198831 A1* | 6/2022 | Coleman | G06T 7/0012 |

FOREIGN PATENT DOCUMENTS

| | | |
|---|---|---|
| CN | 203970352 U | 12/2014 |
| CN | 106019588 A | 10/2016 |
| CN | 106060142 A | 10/2016 |
| CN | 205903239 U | 1/2017 |
| CN | 106388762 A | 2/2017 |
| CN | 106448088 A | 2/2017 |
| CN | 106999337 A | 8/2017 |
| CN | 107174195 A | 9/2017 |
| CN | 107220021 A | 9/2017 |
| CN | 107645921 A | 1/2018 |
| CN | 107680683 A | 2/2018 |
| CN | 108478184 A | 9/2018 |
| CN | 109788901 A | 5/2019 |
| CN | 110547756 A | 12/2019 |
| CN | 110573061 A | 12/2019 |
| CN | 110772218 A | 2/2020 |
| CN | 111699432 A | 9/2020 |
| CN | 111919159 A | 11/2020 |
| CN | 113080842 | 7/2021 |
| JP | 2017136217 A | 8/2017 |
| KR | 20180083069 A | 7/2018 |
| WO | 2016111851 A1 | 7/2016 |
| WO | 2019013563 A1 | 1/2019 |
| WO | 2021022028 A1 | 4/2021 |

OTHER PUBLICATIONS

First Office Action dated Jul. 13, 2022 in Chinese Patent Application No. 202110278476.1, with English translation (18 pages).
Second Office Action dated Jan. 5, 2023 in Chinese Patent Application No. 202110278476.1, with English translation (17 pages).
Third Office Action dated Apr. 26, 2023 in Chinese Patent Application No. 202110278476.1, with English translation (11 pages).
Notice of Allowance dated May 29, 2023 in Chinese Patent Application No. 202110278476.1, with English translation (7 pages).

* cited by examiner

HEAD-MOUNTED VISION DETECTION EQUIPMENT, VISION DETECTION METHOD AND ELECTRONIC DEVICE

CROSS-REFERENCE TO RELATED APPLICATION

This application is a continuation of PCT International Application No. PCT/CN2021/123608 filed on Oct. 13, 2021, which claims priority to Chinese Patent Application No. 202110278476.1, filed to the China National Intellectual Property Administration on Mar. 15, 2021 and entitled "Head-mounted Vision Detection Equipment, Vision Detection Method and Electronic Equipment", the content of which is hereby incorporated by reference in its entirety.

TECHNICAL FIELD

The present disclosure embodiment relates to the technical field of vision detection, in particular to head-mounted vision detection equipment, vision detection method and electronic device.

BACKGROUND

Ophthalmic equipment is necessary for doctor's performance in eye examination. The current ophthalmic equipment, which needs professional operation and high cost, is limited to be employed in hospitals and other medical institutes. Moreover, the ophthalmic equipment has to be operated in a cumbersome way. Patients need to sit next to the testing equipment guided by the doctor, and put eyes on a specific device for seconds or minutes. This is configured to align the patient's eye with the ophthalmic equipment, which is essential for measurement or treatment on the patient's eyes.

The above method of eye examination, however, may deteriorate the vision, because it needs an appointment before the examination between the doctor and the patient, who may delay the detection for reasons like work. And the test may have distortion due to the patient's long-term posture.

Therefore, a new solution is needed to improve the detection equipment from large size, high cost and inconvenient operation.

SUMMARY

It is an object of an embodiment of the present disclosure to provide head-mounted vision detection equipment, vision detection method and electronic device.

According to the first aspect of the present disclosure, there is provided head-mounted vision detection equipment, including a virtual reality headset, a sound collection device and a fundus detection device that are arranged on the virtual reality headset, and a processor. The virtual reality headset is configure to display content to be recognized under control of the processor; the sound collection device is configured to obtain a recognition voice of a wearer for the content to be recognized; the fundus detection device is configured to obtain a fundus image of the wearer; and the processor is configured to acquire the recognition voice and the fundus image.

In at least one exemplary embodiment, the processor is further configured to obtain vision data of the wearer according to the recognition voice and the fundus image; or the equipment further includes a communication device, which is configured to send to a server the recognition voice and the fundus image under the control of the processor, and the server is configured to obtain the vision data of the wearer according to the recognition voice and the fundus image.

In at least one exemplary embodiment, the fundus detection device includes a light detector, which includes a light transmitter and a light receiver; the light transmitter is configured to emit light signals to the eyes of the wearer, and the light receiver is configured to receive the light signals reflected by the eyes of the wearer and form the fundus image according to the light signals received.

In at least one exemplary embodiment, the fundus detection device includes an acoustic wave detector, which includes an acoustic wave transmitter and an acoustic wave receiver; the acoustic wave transmitter is configured to emit acoustic wave signals to eyes of the wearer, and the acoustic wave receiver is configured to receive the acoustic wave signals reflected by the eyes of the wearer and form the fundus image according to the acoustic wave signals received.

In at least one exemplary embodiment, the device further includes an operating handle and a speaker that are used to communicate with the processor that is arranged on the virtual reality headset. The operation handle is provided with multiple operation keys, at least one of which corresponding to at least one control node of the equipment; the speaker is configured to configured to instruct the wearer to action.

In at least one exemplary embodiment, the processor is configured to control the virtual reality headset to perform distance adjustment and switching of the content to be recognized, wherein the processor is further configured to control the fundus detection device to obtain the fundus image of the wearer, which includes: controlling the virtual reality headset to display a focus image so that the wearer can watch the focus image, and controlling the fundus detection device to work after the focus image is displayed.

In at least one exemplary embodiment, the virtual reality headset includes a VR helmet or an AR helmet, which is configured to provide a virtual visual space, and the virtual visual space is used to display the content to be recognized.

In at least one exemplary embodiment, the light transmitter is configured to emit a plurality of light signals to the eyes of the wearer, and the light receiver is configured to receive the plurality of light signals reflected by the eyes of the wearer and generate the fundus image representing texture information of eyeballs, according to strength and wavelength of the plurality of light signals received.

In at least one exemplary embodiment, the acoustic wave transmitter is configured to emit a plurality of acoustic wave signals to the eyes of the wearer, and the acoustic wave receiver is configured to receive the plurality of acoustic wave signals reflected by the eyes of the wearer and generate the fundus image representing texture information of eyeballs according to strength and wavelength of the plurality of acoustic wave signals received.

According to the second aspect of the present disclosure, there is provided a visual detection method based on the head-mounted vision detection equipment, which is executed by the processor, including: controlling the virtual reality headset to display, at different distances, the content to be recognized; controlling the sound collection device to obtain the recognition voice of the wearer for the content to be recognized; controlling the fundus detection device to obtain the fundus image of the wearer; and obtaining the vision data of the wearer according to the recognition voice and the fundus image.

In at least one exemplary embodiment, obtaining the vision data of the wearer according to the recognition voice and the fundus image includes: comparing the recognition voice with the content to be recognized, to obtain first vision data; comparing physiological parameters represented by the fundus image with preset parameters, to obtain second vision data.

According to the third aspect of the present disclosure, there is provided an electronic device including a memory and a processor. The memory is configured to store computer programs; the processor is configured to execute the computer programs to embodiment the any method in the second aspect of the present disclosure.

According to the fourth aspect of the present disclosure, there is provided a computer-readable storage medium, which can be used to store computer programs that are able to carry out any method in the second aspect of the present disclosure, under the control of the processor. One of the advantages of the present disclosure, which is used to conduct self-test of the wearer's vision by displaying the content to be recognized through a virtual reality headset; detecting the recognition ability of the wearer through the combination with a sound collection device; obtaining the fundus image of the wearer through the fundus detection device so as to detect the physiological condition of the wearer's eye, is characterized to be compact, convenient and flexible.

The present disclosure will now be described with reference to the accompanying drawings that illustrate the preferred embodiments of the disclosure, from which its other advantages and features will be evident.

BRIEF DESCRIPTION OF THE DRAWINGS

The drawings are to help explain the principles of the embodiments of the present disclosure together with the description, which is incorporated in the specification and constitutes a part of the specification.

DETAILED DESCRIPTION OF THE EMBODIMENTS

The exemplary embodiments of the present disclosure will now be described in detail with reference to the accompanying drawings. It should be noted that the components, step order, numerical expressions and numerical values set forth in these embodiments should not be limited in the scope of the present disclosure, unless specifically stated.

The following description of at least one exemplary embodiment is actually only illustrative, and in no way serves as any limitation to the present disclosure and its application or usage.

The techniques, methods, and equipment known to those of ordinary skill in relevant fields may not be discussed in detail, which should be regarded as part of the specification where appropriate.

Any specific value should be interpreted as merely exemplary, rather than as a limitation in all the examples shown and discussed herein. Therefore, the exemplary embodiment may have different values in other examples.

It should be noted that similar reference numerals and letters indicate similar items in the following drawings, which do not need to be further discussed in the subsequent drawings if defined in one drawing.

One of the application scenarios of the embodiment of the present disclosure refers to a case where the user with some eye discomfort such as reduced eyesight and presbyopia perform a preliminary self-test of eyesight.

Due to the complexity of traditional vision detection, including the appointment and the complicated detection procedures in the hospital, this present disclosure refers to head-mounted vision detection equipment, a vision detection method and an electronic device to improve the technology in the traditional vision detection.

Figure 1:
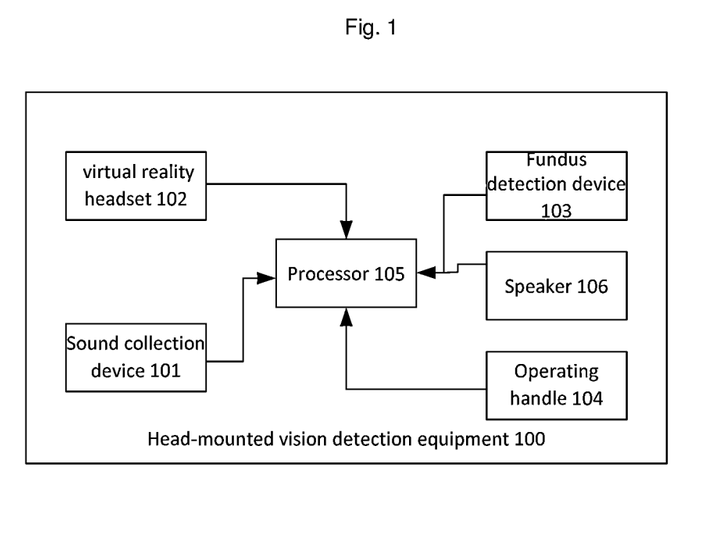
FIG. 1 is a schematic diagram of the structure of the head-mounted vision detection equipment according to an embodiment.

FIG. 1 is provided head-mounted vision detection equipment 100, including a virtual reality headset 102, a sound collection device 101 and a fundus detection device 103 that are arranged on the virtual reality headset 102, and a processor 105. The virtual reality headset 102 is configured to display content to be recognized under control of the processor 105; the sound collection device 101 is configured to obtain a recognition response of a wearer for the content to be recognized; the fundus detection device 103 is configured to obtain a fundus image of the wearer; and the processor 105 is configured to acquire the recognition voice and the fundus image.

In a feasible embodiment, the virtual reality headset 102 can be a VR helmet or an AR helmet, which is configured to provide a virtual visual space, and the virtual visual space is used to display the content to be easily recognized, such as text or images.

The sound collection device 101 can be a voice detector, which is configured to collect the voice information of the wearer which responds the content displayed on the virtual reality headset. For example, the sound collection device will collect the pronunciation of the Chinese character "你好" from the wearer, if the virtual reality headset shows this. It should be noted that the corresponding voice read by the wearer according to the Chinese character may be consistent with or different from the content to be identified, that is to say, as long as the sound collecting device receives the voice collecting instruction sent by the processor, the sound collecting device collects the voice.

Figure 2:
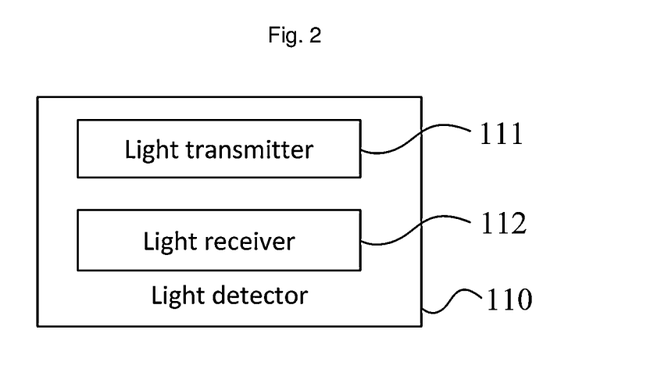
FIG. 2 is a schematic diagram of the structure of light detector of the head-mounted vision detection equipment according to an embodiment.

In another feasible embodiment referring to FIG. 2, the fundus detection device 103 can also be the light detector 110 based on light signals, which is configured to obtain the fundus image of the wearer. The light detector 110 includes a light transmitter 111 and a light receiver 112. The light transmitter 111 is configured to emit light signals to the eyes of the wearer, and the light receiver 112 is configured to receive the light signals reflected by the eyes of the wearer and form the fundus image according to the light signals received.

The light transmitter 111 and the light receiver 112 are both set on the virtual reality headset 102. When in use, the light transmitter 111 emits multiple light signals to eyes of the wearer; the light receiver 112 receives the light signals reflected by eyes of the wearer and generates the fundus image representing the texture information of the eyeball, through the analysis of the strength and wavelength of the light signals received.

Figure 3:
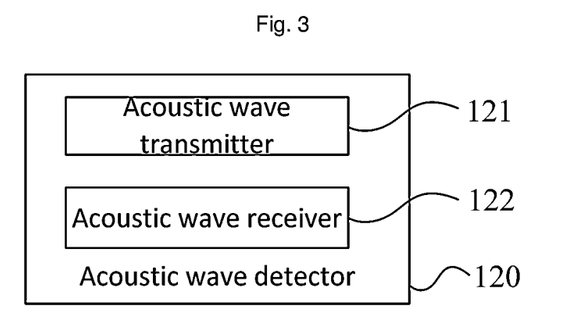
FIG. 3 is a schematic diagram of the structure of acoustic wave detector of the head-mounted vision detection equipment according to an embodiment.

In another feasible embodiment referring to FIG. 3, the fundus detection device 103 can be a acoustic wave detector 120 based on acoustic wave signals, which is configured to obtain the fundus image of the wearer.

The acoustic wave detector 120 includes an acoustic wave transmitter 121 and an acoustic wave receiver 122. The acoustic wave transmitter 121 is configured to emit acoustic wave signals to eyes of the wearer, and the acoustic wave receiver 122 is configured to receive the acoustic wave signals reflected by the eyes of the wearer and form the fundus image according to the acoustic wave signals received.

The acoustic wave transmitter 121 and the acoustic wave receiver 122 are both set on the virtual reality headset 103. When in use, the acoustic wave transmitter 111 emits multiple acoustic wave signals to eyes of the wearer; the acoustic wave receiver 112 receives the acoustic wave signals reflected by eyes of the wearer and generates the fundus image representing the texture information of the eyeball, through the analysis of the strength and wavelength of the acoustic wave signals received.

Something usual in the eyeball may cause different features of the eyeball, including the thickness of the retina, and the curvature radius of the cornea. Therefore, it is evident that the vision can be detected relying on the features showed in the fundus image.

The light detector 110 and the acoustic wave detector 120 can be respectively arranged on a virtual reality headset. Both of them can also be arranged on the same virtual reality headset, which can improve the accuracy of the detection, for the comprehensive analysis based on fundus images obtained by them.

The processor 105 is configured to collect recognition voice and fundus images, and generate the data of wearer's vision based on the analysis of two or three of recognition voice, fundus pictures obtained by light detectors, and fundus images obtained by sound wave detectors.

In a feasible example, the first group of data of wearer's vision can use a percentage or a score showing the consistence between the recognition voice and the content to be recognized, through the comparison between both factors, as an evaluation of wearer's vision.

The second vision data can use a percentage or a score showing the consistence between the physiological parameter and preset parameters based on the comparison between both factors, through which wearer can learn more about their eyes. Physiological parameters refer to the information about physiological characteristics of the eyeball, such as the thickness of the retina and the radius of curvature of the cornea.

In a feasible example, the processor can adjust the distance between the virtual reality headset and the wearer, and change the content displayed in the virtual reality headset to detect wearer's recognition capacity in an overall way, making more exact detection of the vision. Wherein, the distance between the content and the eye can be set with a reference to the medically prescribed distance, which at least includes the farthest and the shortest distance.

In addition, the processor 105 is also configured to control the fundus detection device to obtain the fundus image of the wearer, including: controlling the virtual reality headset to display the image, which is configured to be focused by the wearer to ensure the eyes of the wearer are in appropriate position, to make sure the fundus image standard and accurate, and avoid affecting the authenticity of the fundus image due to the inclination of the eyeballs position.

The processor controls the virtual reality headset to display the image to be focused by wearer before controlling the fundus detection device to collect the fundus image, which can be a virtual image card.

A practical application of this embodiment will now be described, taking the fundus detection device with both the light detector and the acoustic wave detector as an example:

In the case that the head-mounted vision detection equipment of this embodiment is normal in all functions: since someone wears a virtual reality headset, the processor controls the virtual reality headset to randomly display 30-40 different Chinese characters in sequence; the wearer reads the characters under the instructions, which will be recorded by the sound collection device under the control of the processor; the processor will make a comparison with the content to be recognized, and give a score (first vision data). The distance between the eyes and the characters can be adjusted to obtain different results, ensuring a more exact detection result. When in practice, a standard threshold can be set in the processor. Thus if the test score is less than the threshold, there will be a higher risk of vision problems. Taking presbyopia as an example, which means that the lower test score than the threshold means higher risks of presbyopia.

At the moment of acquiring the first vision data, the processor controls the virtual reality headset to display an focus image, which shall be focused by the wearer under the instruction. Controlled by the processor, the light detector to emit light signals to the eyes of the wearer, and the light receiver will receive the light signals reflected by eyes of the wearer. Based on the computer vision algorithms and digital signal processing algorithms, the processor will obtain the physiological parameters in the fundus image including the retinal thickness, corneal curvature radius. Then a comparison shall be made between the obtained physiological parameters and preset parameters, to obtain the second vision data based on the light signals, which indicates the risk of the wearer's presbyopia.

In the same way, the processor controls the acoustic wave detector to emit acoustic wave signals to the eyes of the wearer, and the acoustic wave receiver will receive the acoustic wave signals reflected by eyes of the wearer. Based on the computer vision algorithms and digital signal processing algorithms, the processor will obtain the physiological parameters in the fundus image. Then a comparison shall be made between the obtained physiological parameters and preset parameters, to obtain the second vision data based on the acoustic wave signals, which indicates the risk of the wearer's presbyopia.

When in practice, weighted average calculation shall be made on the first vision data, the second vision data respectively based on light signals and acoustic signals to obtain a comprehensive score, which means a higher risk of presbyopia if it is lower than the standard, and also means a warning of seeing a doctor. Thus the device realizes a self-checking way, with the helmet being compact, convenient, and easy to operate.

Figure 4:
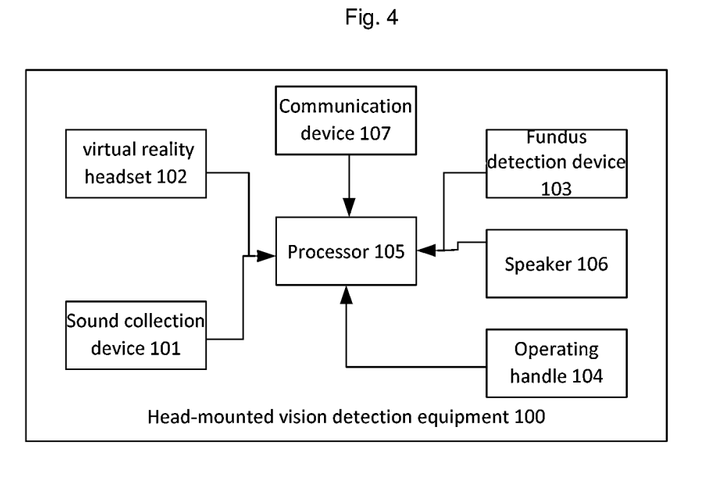
FIG. 4 is another schematic diagram of the structure of the head-mounted vision detection equipment according to an embodiment.

Further, referring to FIG. 4, the head-mounted vision detection equipment in this embodiment includes a communication device 107, which is controlled by the processor 105 to send the recognition voice and the fundus image to the server, which is configured to process and generate the wearer's vision data accordingly, lightening the burden on the computer and improving the calculation efficiency. In addition, the fundus image in this embodiment may be generated by the processor. Specifically, the fundus detecting device collects and transmits the light signal or sound wave signal reflected by the fundus to the processor, which will generate the fundus image based on the transmitted signals.

In an optional example, referring to FIG. 1, the device of this embodiment further includes the operating handle 104 and the speaker 106 that are used to communicate with the processor.

The operating handle 104 is provided with multiple operating keys virtually or physically, at least one of which controls no less one node of the head-mounted vision detection equipment, ensuring the entrance to the corresponding program with a press on the key. For example, when the virtual reality headset is displaying the image, a press on the key could order the processor to control the light detector to emit light signals to the eyes of the wearer.

The speaker 106 is set to instruct the wearer's action. For example, the speaker will issue an instruction of "Please read the characters" under the control of the processor, when the virtual reality headset displays the content to be recognized. And the wearer shall do as the speaker's order.

The present disclosure, conducting self-test of the wearer's vision by a headset which detects wearer's vision based on both the image obtained by the fundus detection device and the wearer's voice obtained by the sound collection device to the content displayed on the helmet, is characterized to be compact, convenient and flexible.

Figure 5:
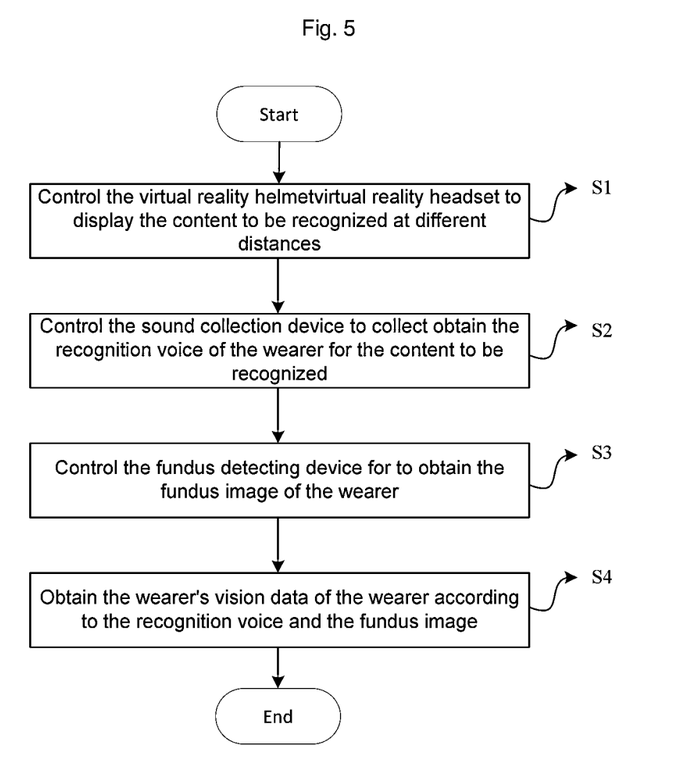
FIG. 5 is a schematic flowchart of a head-mounted vision detection equipment according to another embodiment.

Referring to FIG. 5, this embodiment provides a vision detection method based on the detection device in the foregoing embodiment. The method is executed by the processor in FIG. 1, and the method includes:

S1: Control the virtual reality headset to display the content to be recognized at different distances;

Wherein, the distance between the content and the eye can be set with a reference to the medically prescribed distance, which at least includes the farthest and the shortest distance. For example, the processor controls the virtual reality headset to display 30-40 different Chinese characters first in the virtual space one meter away from the eyes, and then display 30-40 different Chinese characters in a virtual space 1.5 meters away from the eyes. With operation like this for several times, the vision detection will be more exact.

S2: Control the sound collection device to obtain the recognition voice of the wearer for the content to be recognized.

The processor will control the sound collection device to receive the recognition voice of the wearer, who reads out the content displayed on the virtual reality headset according to the instructions on the helmet or from the speaker. The corresponding voice read by the wearer according to the Chinese character may be consistent with or may be inconsistent with the content to be identified, that is to say, as long as the sound collection apparatus receives a sound collection instruction sent by the processor, the sound collection apparatus collects the sound.

S3: Control the fundus detecting device to obtain the fundus image of the wearer.

The fundus detection device includes the light detector and the acoustic wave detector in the above embodiments. The processor controls the light detector to generate the fundus image by using light signals, and/or controls the acoustic wave detector to generate the fundus image by using acoustic wave signals. It should be noted that the processor does not control the light detector and the acoustic wave detector in sequence if they are included in the same fundus detection device.

S4: Obtain the vision data of the wearer according to the recognition voice and the fundus image.

By the comparison between the content recognized from the voice received by the sound collection device and the content displayed on the helmet, the processor obtains the first vision data, which can be recorded as a score. And a standard threshold can be set in the processor in practice. Thus if the test score is less than the threshold, there will be a higher risk of vision problems. Taking presbyopia as an example, which means that the lower test score than the threshold means higher risks of presbyopia.

The processor obtains the second vision data, through the comparison between the preset parameters and the physiological parameters, wherein the physiological parameters represented by the fundus image including the retinal thickness, eye corneal curvature radius, the second vision data based on the light signal is comprehensively obtained by comparing the retinal thickness with a preset parameter and comparing the eye corneal curvature radius with a preset parameter. Taking presbyopia as an example, the second vision data represents the possibility of a wearer obtaining presbyopia.

In a feasible example, weighted average calculation shall be made on the first vision data, the second vision data respectively based on light signals and acoustic signals, for example, the first vision data weighting 0.2, the second vision data based on the light signals weighting 0.4, and the second vision data based on the acoustic wave signals weighting 0.4, a comprehensive score can be obtained according to the weight values, which means a higher risk of presbyopia if it is lower than the standard, and also means a warning of seeing a doctor. Thus the device realizes a self-checking way, with the helmet being compact, convenient, and easy to operate.

In this embodiment, the head-mounted device, conducting self-test of the wearer's vision by a headset which detects wearer's vision based on both the image obtained by the fundus detection device and the wearer's response obtained by the sound collection device to the content displayed on the helmet, is characterized to be compact, convenient and flexible.

Figure 6:
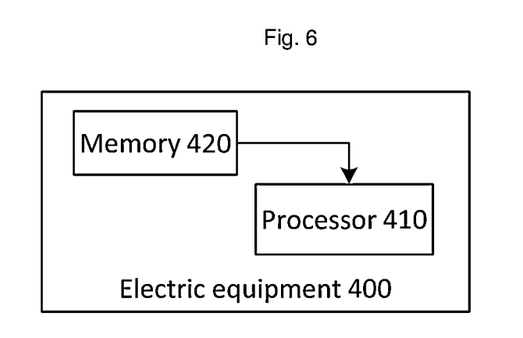
FIG. 6 is a block schematic diagram of an electronic device according to an embodiment.

FIG. 6 is a schematic diagram of the hardware structure of an electronic device according to another embodiment.

As shown in FIG. 6, the electronic device 400 includes the processor 410 and the memory 420. The memory 420 is configured to store an executable computer program, and the processor 410 is configured to execute any of the above methods embodiments under the control of the computer program.

The embodiment may be a system, method and/or computer program product that includes a computer-readable storage medium loaded with computer-readable program instructions for enabling a processor to realize all procedures of the embodiment.

The computer-readable storage medium may be a tangible device that holds and stores instructions used by the instruction execution device. The computer-readable storage medium may be but not limited to, an electrical storage device, a magnetic storage device, an optical storage device, an electromagnetic storage device, a semiconductor storage device, or any suitable combination of the foregoing. More specifically, the computer-readable storage medium can be (not limited to): portable computer disks, hard disks, random access memory (RAM), read-only memory (ROM), erasable programmable read-only memory (EPROM or flash memory), static random access memory (SRAM), portable compact disk read-only memory (CD-ROM), digital versatile disk (DVD), memory stick, floppy disk, mechanical encoding device, the hole card or the protruding structure in the groove with instructions stored thereon, and any suitable combination of the above. The computer-readable storage medium used herein is not interpreted as a transient signal, such as radio waves or other freely propagating electromagnetic waves, electromagnetic waves propagating through waveguides or other transmission media (like the light pulses propagating through fiber optic cables), or electrical signals propagating through wires.

The computer-readable program instructions described herein can be downloaded from a computer-readable storage medium to computing/processing devices or an external computer or external storage device via a network, such as the Internet, a local area network, a wide area network, and/or a wireless network. The network may include copper transmission cables, optical fiber transmission, wireless transmission, routers, firewalls, switches, gateway computers, and/or edge servers. The network adapter card or network interface in each computing/processing device receives computer-readable program instructions from the network, and forwards the instructions for storage in their computer-readable storage medium.

The program instructions of the computer to perform all operations of the embodiment can be assembly instructions, instruction set architecture (ISA) instructions, machine instructions, machine-related instructions, microcode, firmware instructions, status setting data, source code or object code written in one type of programming language or several programming languages, which include object-oriented programming languages such as Smalltalk, C++, and conventional procedural programming languages such as C programming language or some other similar. Computer-readable program instructions can be executed entirely or partly on the user's computer, executed as a stand-alone software package, executed both on the user's computer and a remote computer, or entirely on the remote computer or server implement. The remote computer joining the operation can be connected to the user's computer through any kind of network, including a local area network (LAN) or a wide area network (WAN), or it can be connected to an external computer (connect to the user's computer through the Internet). In some embodiments, an electronic circuit can be customized based on the status of the computer-readable program instructions, such as a programmable logic circuit, a field programmable gate array (FPGA) and a programmable logic array (PLA), to realize all aspects of the present disclosure.

All aspects of the present disclosure are now described with reference to flowcharts and/or block diagrams of methods, devices (systems) and computer program products of the embodiments of the present disclosure. It should be learned that contents in each block or the combination of blocks in the flowcharts and/or block diagrams, can be performed by computer-readable program instructions.

These computer-readable program instructions can be provided to the processors of general-purpose computers, special-purpose computers, or other programmable data processing devices, thereby producing a machine that makes these instructions generate a device that implements the functions/actions in one or more blocks in the flowcharts and/or block diagrams, when executed by the processors of the computer or other programmable data processing devices. These instructions, which make computers, programmable data processing apparatuses, and/or other devices work in a specific manner, can also be stored in a computer-readable storage medium. Thus, the computer-readable medium storing the instructions includes an manufacturing package composed of instructions for implementing the functions/actions in one or more blocks in the flowcharts and/or block diagrams.

It is also possible to load computer-readable program instructions on a computer, other programmable data processing device, or other equipment, to execute a series of operation steps in realizing the functions/actions specified in one or more blocks in the flowcharts and/or block diagrams on those devices.

The flowcharts and block diagrams in the accompanying drawings show the system, method, and the architecture, functions and operations possibly completed by the computer program product in the present disclosure. Each block in the flowchart or block diagram may represent a module, program segment, or part of an instruction, which contains one or more executable instructions for realizing the specified logical function. In some alternative implementations, the functions marked in the block may be realized in an order different from that marked in the drawings. For example, functions in two consecutive blocks can actually be executed substantially in parallel, or in the reverse order, depending on the functions involved. It should also be noted that functions in each block or in the combination of the blocks in the block diagram and/or flowchart, can be implemented by both a dedicated hardware-based system that performs the specified functions or actions, and a combination of dedicated hardware and computer instructions. It is well known to those skilled in the art that the embodiments conducted through hardware, through software, or through a combination of both are all equivalent.

The description of embodiments of the present disclosure is exemplary but not exhaustive. And it is not limited to the disclosed embodiments. And it is obvious for those of ordinary skill in the art to find the modifications and changes in the described embodiments, within the scope of this present disclosure. Terms used herein is intended to best explain the principles and practical applications of the embodiments, or technical improvements in the market, and to enable general skilled in the art to understand the embodiments disclosed herein. The scope of the present disclosure is defined by the appended claims.

The invention claimed is:

1. Head-mounted vision detection equipment, comprising a virtual reality headset, a sound collection device and a fundus detection device that are arranged on the virtual reality headset, and a processor;
   the virtual reality headset is configured to display content to be recognized under control of the processor;
   the sound collection device is configured to obtain a recognition voice of a wearer for the content to be recognized;
   the fundus detection device is configured to obtain a fundus image of the wearer; and
   the processor is configured to acquire the recognition voice and the fundus image.

2. The equipment according to claim 1, wherein the processor is further configured to obtain vision data of the wearer according to the recognition voice and the fundus image; or
   the equipment further comprises a communication device, which is configured to send to a server the recognition voice and the fundus image under the control of the processor, and the server is configured to obtain the vision data of the wearer according to the recognition voice and the fundus image.

3. The equipment according to claim 1, wherein the fundus detection device comprises a light detector;
the light detector comprises a light transmitter and a light receiver;
the light transmitter is configured to emit light signals to eyes of the wearer, and the light receiver is configured to receive the light signals reflected by the eyes of the wearer and form the fundus image according to the light signals received.

4. The equipment according to claim 1, wherein the fundus detection device comprises an acoustic wave detector;
the acoustic wave detector comprises an acoustic wave transmitter and an acoustic wave receiver;
the acoustic wave transmitter is configured to emit acoustic wave signals to eyes of the wearer, and the acoustic wave receiver is configured to receive the acoustic wave signals reflected by the eyes of the wearer and form the fundus image according to the acoustic wave signals received.

5. The equipment according to claim 1, wherein the equipment further comprises an operating handle and a speaker that are used to communicate with the processor that is arranged on the virtual reality headset;
the operation handle is provided with multiple operation keys, at least one of which corresponding to at least one control node of the equipment; and
the speaker is configured to instruct the wearer to act.

6. The equipment according to claim 1, wherein the processor is further configured to control the virtual reality headset to perform distance adjustment and switching of the content to be recognized.

7. The equipment according to claim 1, wherein the virtual reality headset comprises a VR helmet or an AR helmet, which is configured to provide a virtual visual space, and the virtual visual space is used to display the content to be recognized.

8. The equipment according to claim 3, wherein the light transmitter is configured to emit a plurality of light signals to the eyes of the wearer, and the light receiver is configured to receive the plurality of light signals reflected by the eyes of the wearer and generate the fundus image representing texture information of eyeballs, according to strength and wavelength of the plurality of light signals received.

9. The equipment according to claim 4, wherein the acoustic wave transmitter is configured to emit a plurality of acoustic wave signals to the eyes of the wearer, and the acoustic wave receiver is configured to receive the plurality of acoustic wave signals reflected by the eyes of the wearer and generate the fundus image representing texture information of eyeballs according to strength and wavelength of the plurality of acoustic wave signals received.

10. A visual detection method based on the head-mounted vision detection equipment of claim 1, wherein the method is executed by the processor, and the method comprises:
controlling the virtual reality headset to display, at different distances, the content to be recognized;
controlling the sound collection device to obtain the recognition voice of the wearer for the content to be recognized;
controlling the fundus detection device to obtain the fundus image of the wearer; and
obtaining the vision data of the wearer according to the recognition voice and the fundus image.

11. The method according to claim 10, wherein obtaining the vision data of the wearer according to the recognition voice and the fundus image comprises:
comparing the recognition voice with the content to be recognized, to obtain first vision data;
comparing physiological parameters represented by the fundus image with preset parameters, to obtain second vision data.

12. An electronic device, comprising a memory and a processor, the memory is configured to store computer programs; the processor is configured to execute the computer programs to implement the method of claim 10.

13. A computer-readable storage medium, which is used to store computer programs that are able to carry out claim 10, under the control of the processor.

14. The equipment according to claim 1, wherein the processor is further configured to control the fundus detection device to obtain the fundus image of the wearer, which comprises: controlling the virtual reality headset to display a focus image so that the wearer can watch the focus image, and controlling the fundus detection device to work after the focus image is displayed.

15. The equipment according to claim 1, wherein the focus image comprises a virtual image card.

16. The equipment according to claim 1, wherein the processor is further configured to control the virtual reality headset to perform distance adjustment of the content to be recognized according to a medical regulated distance corresponding to eye data.

17. The method according to claim 11, wherein the physiological parameters represented by the fundus image comprises at least one of:
retinal thickness, corneal radius of curvature.

18. The method according to claim 11, wherein obtaining the vision data of the wearer according to the recognition voice and the fundus image comprises:
performing weighted summation on the first vision data and the second vision data;
determining the vision data of the wearer based on a summation result.

19. An electronic device, comprising a memory and a processor, the memory is configured to store computer programs; the processor is configured to execute the computer programs to implement the method of claim 11.

20. A computer-readable storage medium, which is used to store computer programs that are able to carry out the method of claim 11, under the control of the processor.

* * * * *